US008835703B2

(12) United States Patent
Morschbacker

(10) Patent No.: US 8,835,703 B2
(45) Date of Patent: Sep. 16, 2014

(54) METHOD FOR THE PRODUCTION OF ONE OR MORE OLEFINS, AN OLEFIN, AND A POLYMER

(75) Inventor: Antonio Luiz Ribeiro De Castro Morschbacker, Porto Alegre (BR)

(73) Assignee: Braskem S.A., Camacari (BR)

( * ) Notice: Subject to any disclaimer, the term of this patent is extended or adjusted under 35 U.S.C. 154(b) by 570 days.

(21) Appl. No.: 12/517,707

(22) PCT Filed: Nov. 30, 2007

(86) PCT No.: PCT/BR2007/000328
§ 371 (c)(1),
(2), (4) Date: Jun. 4, 2009

(87) PCT Pub. No.: WO2008/067627
PCT Pub. Date: Jun. 12, 2008

(65) Prior Publication Data
US 2010/0069691 A1    Mar. 18, 2010

(30) Foreign Application Priority Data
Dec. 5, 2006 (BR) .................................. 0605173-1

(51) Int. Cl.
| C07C 1/04 | (2006.01) |
| C07C 11/04 | (2006.01) |
| C10G 3/00 | (2006.01) |
| C10J 3/66 | (2006.01) |
| C07C 11/06 | (2006.01) |
| C07C 29/151 | (2006.01) |
| C07C 11/08 | (2006.01) |
| C12P 7/10 | (2006.01) |

(52) U.S. Cl.
CPC .... *C07C 29/1518* (2013.01); *C10G 2300/1044* (2013.01); *C10G 2300/1014* (2013.01); *C10J 2300/0916* (2013.01); *C10G 2400/20* (2013.01); *C07C 11/04* (2013.01); *C10G 2300/4025* (2013.01); *C10G 3/00* (2013.01); *C10J 3/66* (2013.01); *C10J 2300/1284* (2013.01); *C07C 11/06* (2013.01); *C10G 2300/1003* (2013.01); *Y02E 50/16* (2013.01); *Y02E 50/18* (2013.01); *C10J 2300/1665* (2013.01); *C10J 2300/0959* (2013.01); *C10G 2300/1025* (2013.01); *Y02E 50/343* (2013.01); *C10G 2400/22* (2013.01); *C07C 11/08* (2013.01); *C12P 7/10* (2013.01); *Y02E 50/32* (2013.01)
USPC ........... 585/240; 585/242; 585/324; 585/638; 585/639; 585/640

(58) Field of Classification Search
USPC .......................... 585/240, 242, 324, 638–640
See application file for complete search history.

(56) References Cited

U.S. PATENT DOCUMENTS

| 5,714,662 A | 2/1998 | Vora et al. |
| 6,534,692 B1 | 3/2003 | Barger et al. |

(Continued)

FOREIGN PATENT DOCUMENTS

| EP | 0 448 000 A1 | 9/1991 |
| WO | WO-03/018723 A1 | 3/2003 |
| WO | WO-2004/060841 A1 | 7/2004 |

*Primary Examiner* — Brian McCaig
(74) *Attorney, Agent, or Firm* — Birch, Stewart, Kolasch & Birch, LLP

(57) ABSTRACT

The present invention describes a method for the production of one or more olefins from the residue of at least one renewable natural raw material. The present invention is advantageously related to a method that is integrated with a processing method for processing renewable natural agricultural raw materials for the production of propylene, and optionally of ethylene and butylene, mainly from the residues of the processed renewable natural agricultural raw material. The propylene is obtained from the gasification reaction of the lignocellulosic materials and of other organic products contained in the raw material residues, followed by the formation of methanol and its subsequent transformation into propylene, where this route may further generate ethylene and/or butylene as by-products.

20 Claims, 1 Drawing Sheet

(56) References Cited

U.S. PATENT DOCUMENTS

| | | |
|---|---|---|
| 6,740,791 B2 * | 5/2004 | Kuechler et al. ............... 585/639 |
| 2004/0116757 A1 * | 6/2004 | Van Egmond et al. ....... 585/324 |
| 2004/0180971 A1 | 9/2004 | Inoue et al. |
| 2005/0112739 A1 * | 5/2005 | Golubkov .................... 435/161 |
| 2010/0275509 A1 * | 11/2010 | Sakuma et al. ................ 44/438 |

* cited by examiner

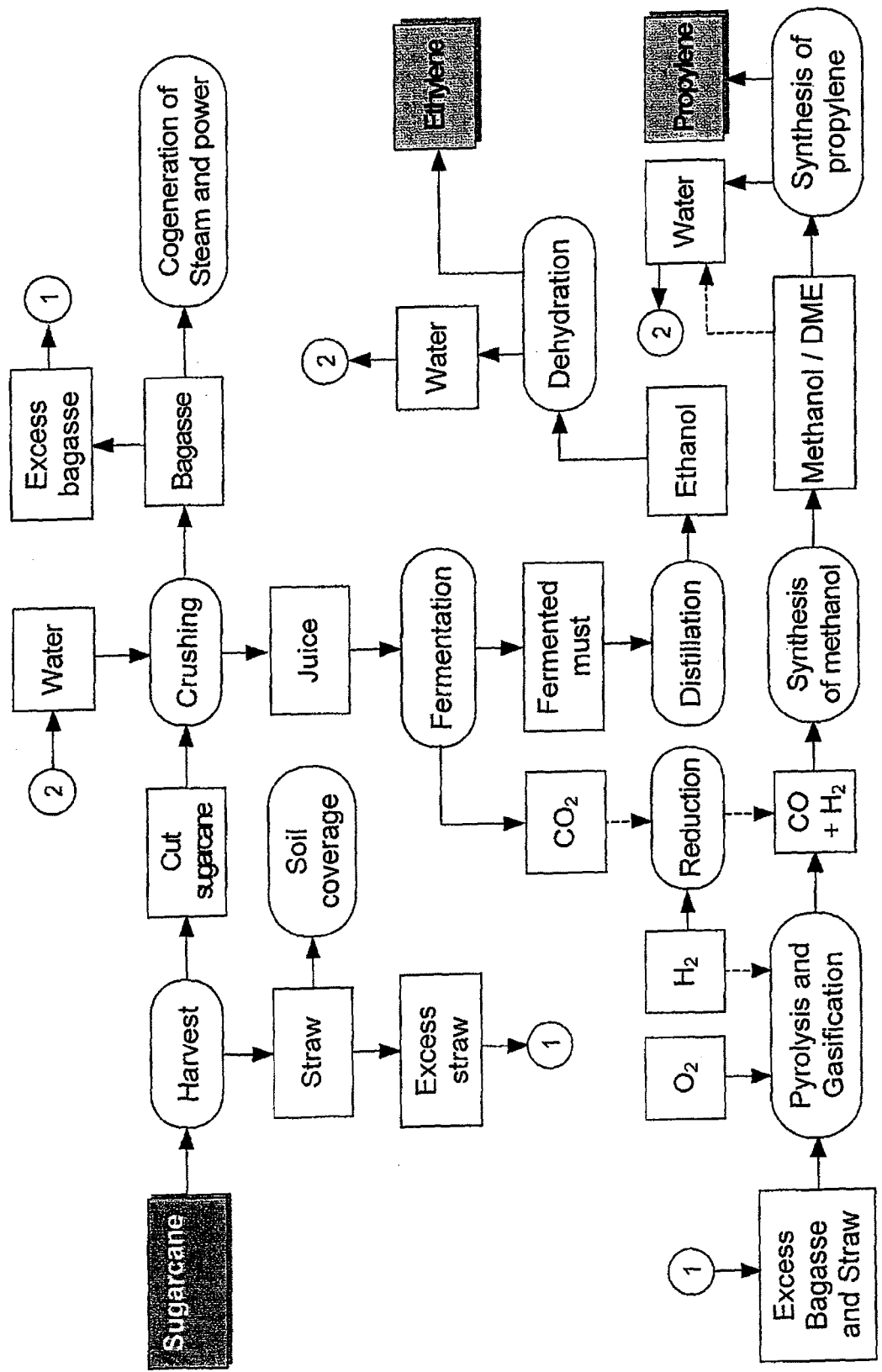

METHOD FOR THE PRODUCTION OF ONE OR MORE OLEFINS, AN OLEFIN, AND A POLYMER

FIELD OF THE INVENTION

The present invention refers to a method for the production of one or more olefins from the residue of at least one renewable natural raw material. Advantageously, the present invention refers to a method that is integrated with a method for processing renewable natural agricultural raw materials for the production of propylene, and optionally, of ethylene and butylene, mainly from the residues of the processed renewable natural agricultural raw material. The olefin(s) is/are obtained from the gasification reaction of the lignocellulosic materials and/or other organic products comprised in the residues of the raw material, followed by the formation of methanol and its subsequent transformation, directly or indirectly from the dimethyl ether intermediate, into propylene, this route being additionally able to provide the generation of ethylene and/or butylene as co-products.

DESCRIPTION OF THE PRIOR ART

The propylene is obtained chiefly as a by-product of petroleum refining, by catalytic or thermal cracking, or as a co-product in the production of ethylene from natural gas (Propylene, Jamie G. Lacson, CEH Marketing Research Report-2004, Chemical Economics Handbook-SRI International).

The propylene constitutes one of the main blocks in the synthesis of petrochemical products, and may be used as raw material for the production of a wide variety of polymers and intermediates. Among the main derivatives of propylene there are included polypropylene and its copolymers, n-butanol and isobutanol obtained via Oxo synthesis, acrylonitrile, propylene oxide, isopropanol, cumene, acetone, epichlorohydrin, acrylic acid and a series of products with a wide variety of possible applications.

Historically, the demand for propylene has been growing at a faster rate than the demand for ethylene, mainly due to the unceasing growth of the demand for polypropylene, its main derivative. Since the production of the propylene is based on natural gas and petroleum and the propylene/ethylene ratio obtained via these routes has a maximum limit in relation to the propylene that can be produced, the offer of propylene has been increasing at a lower rate than the demand thereof. In addition, more than 25% of the production of ethylene scheduled for the period between 2003 and 2006 was based on the use of natural gas as feedstock, and this route usually produces a low amount of propylene. Therefore, there is a need of new alternative routes to produce the amount of propylene required to meet the increasing demand for this product.

The use of new technological routes for the production of propylene, using a wide range of raw materials, has recently been subjected to close consideration. These routes, together with the conventional routes, are evaluated in the study "Technology Developments in Propylene and Propylene Derivatives", Nexant—December 2003. This study reports the following alternative routes:

Olefin metathesis: The production of propylene from ethylene by metathesis provides yield levels below 90%. Therefore, the cost of production of the propylene will be higher than that of the ethylene, justifying the use of this route only in cases where the cost of the ethylene is low or where the propylene demand level remunerates its higher value.

Olefin interconversion: This route is based on catalytic cracking of hydrocarbon streams with 4 and 5 carbon atoms. It is only justifiable in locations where these streams are available in high volumes.

Production via Methanol: This route evidences a relatively higher capital cost and is only justifiable in a case of availability of natural gas at low cost. Additional details concerning the production of olefins via methanol produced in high-volume production units from low-cost natural gas may be obtained in the references, "UOP Methanol to Olefins", Abe Gelbein, PEP Review 2001-11, September 2003, SRI International and "Methanol to Propylene by the Lurgi MTP Process", David Netzer, PEP Review 98-13, August 2002, SRI International.

The ethylene is an olefin that is mainly produced as a by-product of petroleum refining, by steam reforming or catalytic cracking. One other route employed in its production consists in the recovery and dehydrogenation of the ethane contained in natural gas.

The ethylene is used as raw material for an infinite variety of chemical products. Among these there should be mentioned the polyethylene and copolymers thereof, PVC (Polyvinyl Chloride), polystyrene, PET (Polyethylene Terephthalate), ethylene oxide, ethylene glycol, ethanol, vinyl acetate and n-propanol.

On the other hand, the global interest for organic products from renewable sources has increased greatly in recent years, particularly in the case of plastics. The preferred use of products obtained from natural products over those obtained from fossil sources of raw materials has been gaining increasingly wide acceptance as constituting a viable form of reducing the growing concentration of carbon dioxide in the atmosphere and thereby combating in an effective manner the intensification of the greenhouse effect. The products obtained from natural materials may be certified as to their renewable carbon content, according to the methodology described in the technical standard ASTM D 6866-06, "Standard Test Methods for Determining the Biobased Content of Natural Range Materials Using Radiocarbon and Isotope Ratio Mass Spectrometry Analysis".

In his work, Romani Narayan (Ramani Narayan, Michigan State University, Biobased & Biodegradable Polymer Materials: Rationale, Drivers, and Technology Exemplars, Presented at the National American Chemical Society, Division of Polymer Chemistry meeting, San Diego (2005); ACS Symposium Ser (An American Chemical Society Publication) 939 June 2006) explains the principles of the methodology according to the ASTM D 6866-06 standard, which employs $^{14}C$ signature for identifying the carbon which comes from renewable natural sources (Biobased Carbon) in a product and for quantifying the contents thereof. Subsequently, he classifies as biomaterials, or materials resulting from renewable natural sources, the organic products which contain carbon undoubtedly derived from biological sources (non-fossil), and emphasizes their importance as an alternative to the old materials, exclusively based on raw material resources derived from petroleum.

The most known examples among industrial products obtained from natural materials are the fuels of natural origin, such as bio-ethanol or bio-diesel. Other alternatives already available in the market are biopolymers, such as poly(lactic acid) and polyhydroxybutyrate, that may be obtained from sugar or from starch. The biopolymers evidence high growth potential, but are still limited in terms of their properties and entail a higher production cost, which fact inhibits a wider application thereof. More detailed information in this respect may be obtained in "Biodegradable Polymers", Gregory M.

Bohlmann, CEH Marketing Research Report-2004, Chemical Economics Handbook-SRI International.

The ethanol derived from biological sources, known as bio-ethanol, is obtained by fermentation of the sugars found in crops such as sugarcane or from hydrolyzed starch derived from crops such as corn. Other products commercially produced by fermentation are, for example, lactic acid, n-butanol, acetone, and even polymers such as polyhydroxyalkanoates.

The production of ethylene based on the dehydration of ethanol is a widely known process that was commercially exploited in only a few industrial units. Additional details concerning this technology may be found in the study "Ethylene from Ethanol", Harold W. Scheeline and Ryoji Itoh, PEP Review 79-3-4, January 1980, SRI International, in patent documents Nos. U.S. Pat. No. 4,232,179, U.S. Pat. No. 4,234,752, U.S. Pat. No. 4,396,789 and U.S. Pat. No. 4,529,827 and in patent application No. WO 2004/078336. Although this route is still not very competitive, the constantly increasing prices of petroleum by-products, in addition to the continuing decrease of the ethanol production costs, might come to render the same a competitive alternative for the production of ethylene. Therefore, using this technology, it is possible to produce ethylene-based polymers obtained from renewable carbon sources, either integrally therefrom as in the cases of polyethylene and PVC, or partially as in the cases of polystyrene or PET.

One of the motives for the low competitiveness of this technology resides in the fact that the production of ethylene from dehydration of ethanol presents the significant disadvantage of low yield from the total carbon produced by the renewable natural agricultural raw materials used.

In practice, only slightly less than 20% of the organic carbon produced in the cultivation of sugarcane, for example, is transformed into ethylene, the desired end product. The poor reutilization of the bagasse and the leaves of the sugarcane, the inefficient extraction of the sugarcane juice, the formation of by-products during fermentation, particularly carbon dioxide, constitute the main factors that contribute to such poor yield.

The reutilization of the carbon dioxide generated as a by-product in the fermentation is not much employed in large scale, notwithstanding its high purity and extremely low cost. The exceedingly small number of cases of commercial utilization consist, for example, in the use thereof for the production of carbonated soft drinks or the application thereof in pre-treatment for clarification of the sugarcane juice, however the large majority of carbon dioxide obtained as a by-product of alcoholic fermentation is simply emitted to the atmosphere.

As to the reutilization of the bagasse and/or the straw, the main destination thereof, when applied, consists in the cogeneration of electrical power and steam. However, its use can be much more effective if such residues are partially directed to the production of high value products.

The absolute majority of the lines of research presently under development aimed at the reutilization of agricultural lignocellulosic residues, such as for example of sugarcane bagasse, sugarcane straw, corn straw, wheat straw and rice straw, corn cobs and wood kindling, consists in the development of the hydrolysis of those materials in sugars to be fermented. The main components that comprise those materials are cellulose, hemicellulose and lignin, which presence in the composition in terms of weight percentage of the majority of types of biomass is about 45%, 35% and 20%, respectively. The hydrolysis of the cellulose and hemicellulose may be realized by either acidic or enzymatic route and produces various sugars, like glucoses and xylose, among others, but the lignin is wasted. In addition, some of the sugars obtained in the hydrolysis, such as the xylose, are not fermented by the microorganisms traditionally employed in the production of ethanol. The enzymatic hydrolysis further involves a high production cost due to the high price of the enzyme. The acidic hydrolysis is less costly, but requires the use of noble materials in the equipment and entails the inconvenience of generating phenolic compounds that originate from the hydrolysis of the lignin and are deleterious to the subsequent fermentation step.

One alternative that is still not very widely used for reutilization of such lignocellulosic materials consists in the transformation thereof into synthesis gas (a mixture of CO and $H_2$). Using that process, practically all the carbon content of any form of organic matter can be transformed into carbon monoxide.

In spite of the fact that the development of technologies for gasification of lignocellulosic materials and other types of biomass has been occurring with increasing intensity since the beginning of the 1970's, the large-scale application thereof is still incipient. The main purpose driving this development is the obtainment of a gas with high caloric power capable of being burned directly in gas turbines, which latter provide much more efficiency in the generation of electrical power than the burning of the fuel in boilers for producing steam and subsequently generating power using the steam produced in this manner.

Normally, the synthesis gas is produced from fossil carbon sources such as coal, naphtha or natural gas. However, several renewable products may also be used as carbon sources for the production of the synthesis gas. Some examples of useful renewable raw materials include charcoal, wood or agricultural residues such as sugarcane bagasse, rice straw or glycerol. The purification of the synthesis gas, with removal of the ashes, oils and other impurities, is an important step to allow the use thereof for subsequent production of liquid fuels and chemical products, as proposed in patent application No. US 2004/0220285.

There are several processes presently under development for the gasification of biomass. Some of these processes contemplate a prior pyrolysis step and the vapors resulting from this step are subjected to reaction at high temperatures with steam and with controlled amounts of oxygen to produce the mixture of carbon monoxide and hydrogen at the desired ratio and also to supply power to drive the process.

Other processes are conducted in the form of a single stage in a gasification reactor. One characteristic that is common to all processes is that they require the use of oxygen, as the use of air promotes an undesirable formation of nitrogen oxides. Examples of processes for transforming lignocellulosic materials and other types of biomass into carbon monoxide and hydrogen are presented in Brazilian patent document No. PI 98132920 and in patent applications Nos. US 2004/0180971, US 2004/0261670 and WO 2005/047436.

Subsequently, the ratio of the carbon monoxide and hydrogen components may be adjusted by means of the addition of water or carbon dioxide, as taught in patent document No. U.S. Pat. No. 6,254,807 or by the addition of hydrogen as described in patent application No. WO 83/04270.

One characteristic held in common by various types of biomass is their high residual moisture, which constitutes an inconvenient factor for the gasification process. In U.S. Pat. No. 5,695,532 there is described an integrated gasification process wherein the humidity of the biomass is adjusted to the required values in drying vessels.

Further details regarding the biomass gasification technologies may be obtained from the study "Biomass Gasification", Ronald G. Bray, PEP Report No. 258, November 2005, SRI Consulting.

One additional means of producing the synthesis gas consists in reducing the carbon dioxide using organic materials, as described in patent documents Nos. U.S. Pat. No. 3,850,588 and U.S. Pat. No. 4,583,993, or with hydrogen as described in patent documents Nos. U.S. Pat. No. 3,479,149, U.S. Pat. No. 4,758,249, U.S. Pat. No. 5,346,679 and U.S. Pat. No. 5,496,530.

However, in spite of the innumerable developments achieved to date, there is still no commercial unit in operation for the production of synthesis gas from biomass or by reutilization of carbon dioxide, the main reason for such fact being the cost of the process as a whole, which is still high.

Furthermore, the teachings anticipated in the prior art do not provide any description relative to the production of polypropylene and its copolymers from renewable natural raw materials and/or residues thereof. The thus produced bio-polypropylenes, contrary to the majority of known biopolymers, have a low production cost and evidence clearly adequate properties for an immense variety of applications.

OBJECTS OF THE INVENTION

In view of what has been set forth above, one object of the present invention is to provide a method for the production of one or more olefins from the residue of at least one renewable natural raw material.

One other object of the invention consists in providing a method for the production of one or more olefins, integrated with a method for processing renewable natural agricultural raw materials.

One other object consists in the provision of an integrated process that is inexpensive, simple, provides high energy and material effectiveness and high yield.

One other object consists in the provision of an integrated process allowing the obtainment of propylene and optionally, of ethylene and butylene, produced from renewable natural raw materials.

One other object consists in the provision of propylene by-products, and optionally of ethylene and butylene by-products, such as polypropylene and polyethylene, produced from renewable and natural raw materials, as evidenced by the test method prescribed in standard ASTM D 6866-06.

SUMMARIZED DESCRIPTION OF THE INVENTION

The present invention discloses a method for the production of one or more olefins from residue of at least one renewable natural raw material, preferably integrated with a method for processing renewable natural agricultural raw materials. More specifically, the present invention refers to a method, preferably an integrated method, for the production of propylene, and optionally of ethylene and butylene, from the residue of one or more renewable natural raw materials, derived, among others, from the process of production of sugar, starch, paper and pulp, ethanol, n-butanol, acetone, lactic acid, butyric acid, polyhydroxyalkanoates and/or ethylene, this latter generated by dehydration of the ethanol resulting from the fermentation of the hydrolyzed starch or sugar. According to the present invention, the olefin(s) is/are obtained from the gasification reaction of the lignocellulosic materials and/or other organic products present in the residues of renewable natural raw material, followed by the formation of methanol and its subsequent transformation, either directly or indirectly from the intermediate dimethyl ether, into propylene, where such route may further generate ethylene and/or butylene as co-products.

The integrated process preferably used for the production of one or more olefins according to the present invention is simple and may be advantageously used in locations having large availability of renewable natural agricultural raw materials, rich in sugars and/or starch and in lignocellulosic materials, such as sugarcane, corn or sorghum.

Optionally, other renewable natural raw materials may be used as a source of sugars, starch, lignocellulosic materials, vegetable oils, animal fats or of other materials such as, among others, beet, manioc, wheat straw and rice straw, wood kindling, glycerol, bio-diesel production residue containing glycerol, among others.

The integrated process of the present invention evidences as a relevant characteristic the integration of material and energy streams among the employed routes, with the consequent production, from the same quantity of agricultural raw material, of substantially larger amounts of products, due to better usage of energy and waste products, in consequence of the synergies between the processes employed herein.

The method of production according to the present invention is further particularly suitable for the production of ethylene and propylene at low cost from renewable raw materials, with the obtainment of the derivatives thereof, such as polyethylene and polypropylene of natural origin, constituting a relevant aspect of the present invention.

DESCRIPTION OF THE FIGURES

The advantages and characteristics of the present invention will be better evidenced by the description of the preferred embodiments, given as example and not for purposes of limitation, and by the FIGURE referring thereto, wherein:

The FIGURE shows a block diagram of the integrated method for the production of olefins according to the present invention based on the use of processed sugarcane as raw material.

DETAILED DESCRIPTION OF THE INVENTION

The method of the present invention consists in the production of one or more olefins from the residue of at least one renewable natural raw material, preferably integrated with a method for processing renewable natural agricultural raw materials.

More specifically, the present invention refers to a method, preferably consisting in an integrated process, for the production of propylene, and optionally of ethylene and butylene, from one or more residues derived from the processing of renewable natural agricultural raw materials.

There should be understood as constituting residues of at least one renewable natural raw material the residues originated from the processing of agricultural crops or even urban or industrial organic residues or those originating from fishing, animal breeding and mining activities, provided that they can be gasified, that they exhibit a high content of one or more components among sugars, starch, lignocellulosic components, oils, fats, or other organic materials. The reutilization of said residue is optionally integrated with the method used for processing said raw material, such that the residue generated in the method of processing of the renewable natural agricultural raw material is subsequently directed to the process for the production of one or more olefins according to the present invention.

The residues of renewable natural agricultural raw materials that are preferably used in the method for the production of one or more olefins according to the present invention originate from sugarcane, corn or sorghum, such as, for example, sugarcane bagasse, sugarcane straw, corn straw, corn cobs and sorghum straw. Optionally, there may be used the residues of other agricultural crops, urban or industrial residues, as well as residues originating from fishing, animal breeding or mining activities, such as, among others, beet, manioc, wheat or rice straw, peanut shells or coconut shells, wood kindling, wood chips or sawdust, charcoal, wax palm [*Carnaúba*] leaves, babassu palm [*Babacú*] residues, various types of grass, leaves and branches of soy plants, residues of the process of production of vegetable oils, such as filtercakes obtained from the production of oils of soy, of castor oil plant and of other oleaginous plants, vegetable oils after use, animal fats, algae, recycled paper and paperboard, lignin and other residues from the paper and pulp industry originating from crops such as eucalyptus and pine, garbage, biogas derived from fermentation, glycerol, or residues containing glycerol, shellfish shells or bird feathers.

The renewable natural raw material advantageously employed in the present invention is any raw material originating from agricultural crops that are simultaneously rich both in starch and/or sugar and in lignocellulosic materials, such as sugarcane, corn or sorghum.

In the case of use of sugarcane as the agricultural raw material, the harvest thereof took place, until a few years ago, almost exclusively after the burning of the sugarcane on the field, in order to eliminate the leaves and thereby allow the sugarcane to be cut manually. Recently, the harvest of sugarcane has been increasingly made by mechanized cutting, which dispenses the burning. This procedure reduces the environmental impact of the harvesting process, not only by eliminating carbon dioxide emissions, but also due to avoiding the soot produced in the process. With the mechanized harvesting, a new carbon source becomes available from the sugarcane, consisting in the straw originating from the leaves and the tip of the sugarcane plant, which constitute between 12 and 14% by weight of the sugarcane employed. The trend for the coming years points to an increasing use of mechanical harvesting of the sugarcane until such procedure comes to comprehend practically the whole production thereof.

When there is employed mechanized harvesting, a portion of up to 50% of the straw originating from the leaves may be used as dead cover for the soil, to protect the same from the sunshine and rain, contributing to maintain the moisture thereof and to prevent its erosion.

The mechanically harvested cane is loaded onto flatbed loaders packaged in bales and is shipped to the sugar and/or alcohol producing facility for subsequent processing. This processing may comprise the processes of crushing or diffusion, with the extraction of the sugarcane juice being performed with the aid of water and there being produced bagasse.

In turn, the excess sugarcane straw (50% or more of the original straw) may also be conveyed from the field to the location where it will be subsequently processed. Both the straw and the bagasse are materials that have a high content of lignocellulosic components.

The harvest of corn is realized by a rather similar process. This operation is also preferably realized using a mechanical harvester, whereby the corn cob is separated from the culm and leaves and is shelled by separation of the grains from the cob and the straw. The corn grain, which is rich in starch, is directed to the production of alcohol and/or other fermentation products, upon prior hydrolysis, and of other starch derivatives, thereby having a value that is much greater than that of the other components of this crop, such as the culm, the leaves, the straw and the cob, that are rich in lignocellulosic materials and that are treated as waste products.

The lignocellulosic components mentioned herein should be understood to comprise lignin, hemicellulose and cellulose. The lignin is a cross-linked macromolecule, highly hydrophobic, comprised of aromatic elements derived from phenol. The cellulose is a crystalline polysaccharide of non-cross-linked long chain $(C_6H_{10}O_5)_n$ whose monomeric units, glucose, are interlinked by $\beta$1-4 bonds. These bonds are harder to hydrolyze than the $\alpha$1-4 bonds present between the glucose molecules that constitute the polymeric chain of the starch. The hemicellulose is a branched short chain polysaccharide heteropolymer with an amorphous structure and is easier to hydrolyze than cellulose. Among the monomers that constitute the same there are included, in addition to glucose, xylose (its main component), mannose, galactose, rhamnose and arabinose.

In general terms, the lignocellulosic components are usually employed in cogeneration of steam and electrical power to meet the requirements of the production process. Eventual excesses of these components may be used to generate additional energy for commercialization or may be used to supply energy to other types of industries, such as for the manufacture of ceramics, or even for animal feeding.

The bagasse is the main source of energy for the processes that make use of the sugarcane as raw material. Its participation in the total weight of the sugarcane corresponds to approximately 14% in the form of fibers present in its culms. Its energetic content exceeds the requirements of the processes, particularly in the case of ethanol production, generating an excess of bagasse. The burning of bagasse in high-pressure, high-performance boilers is being increasingly adopted, thereby allowing the generation of a larger amount of excess bagasse, which may reach 30% or more of the total amount of bagasse generated. One possible alternative that would be even more energy-effective consist in the generation of synthesis gas from the bagasse and the direct burning of the same in gas turbines. The adoption of this alternative might increase even further the availability of excess bagasse to be used as raw material for the integrated method of the present invention.

Although the sugarcane harvest lasts for approximately 6 months, the excess bagasse may be stored, allowing the subsequent use thereof as raw material through almost the whole year. Furthermore, even if the excess bagasse from a sugar mill or an alcohol distillery is not sufficient to meet the consumption requirements of a unit that demands significant amounts of lignocellulosic materials as raw material, it is always possible to use bagasse and straw from more than one unit to meet the required volumes, or even to use residues originating from other crops.

In the case of the sugarcane, the straw originated from the leaves removed by mechanized harvesting is used as dead cover for the soil, in order to protect the same from the effects of sunshine and rain, contributing to conserve its moisture and to prevent its erosion. However, the amount required to provide such protection to an effective level corresponds to 50% or less of the amount of straw generated in the mechanized harvesting process. The excess amount may be directed to other uses, such as cogeneration of energy or, preferentially, to the production of high-value derivatives.

One of the objectives of the preferred embodiment of the present method is the energy integration of the route of production of sugar/starch, of ethanol, and optionally of ethylene, with the route of gasification and production of olefins, in order to achieve an economy in the use of the lignocellulosic residues in the cogeneration of energy, allowing the obtainment of a larger amount of excess products to be used as raw material for this second route, thereby maximizing the possibility of obtainment of a product of much higher value, such as propylene.

In addition to this energy integration, the reutilization, for generating one or more olefins, of the excess straw and bagasse generated in the processes of harvest and production of sugar, starch and derivatives thereof, preferably from sugarcane and from corn, constitutes one of the characteristics of the present integrated method.

The bagasse obtained after the extraction of the sugarcane juice has a residual moisture content of about 50% by weight. This value is however higher than the values required for the gasification process, which should correspond to 20% by weight or less. The humidity of the straw is lesser, about 25% by weight, but preferably the same should be used as feedstock at lower humidity levels. The utilization of some higher temperature streams generated in the method of the present invention enables the supply of the necessary heat to reduce the residual moisture of the bagasse and straw to the levels required in the gasification process.

The sugarcane juice obtained by the crushing or diffusion process, after the suitable treatment for purification thereof, is directed to the production of sugar and its derivatives, such as ethanol. In parallel, the corn grain can also be directed to the production of starch and derivatives thereof, and may also be used for the production of ethanol, upon prior hydrolysis of the starch.

Various routes of obtainment of the ethanol from the fermentation of sugar or starch are possible, depending on the composition of the biomasss used for that purpose.

In the case of raw materials rich in starch—such as, for example, corn, wheat or manioc—the method comprises the hydrolysis of the starch with the formation of a glucose-rich medium, addition of nutrients and subsequent fermentation using a suitable microorganism.

In the case of raw materials with high sugar content, such as the sugarcane, the fermentation can be provided directly from the juice upon adjustment of the concentration of sugars and of the pH of the medium and addition of nutrients.

In a preferred embodiment of the invention, the raw material is comprised of materials rich in sugars or starch, and in the fermentation there is used the *Saccharomyces cerevisiae* yeast, providing the ethanol as the product and carbon dioxide ($CO_2$) as the main by-product. Other types of microorganisms may be alternatively used in the fermentation process.

Other productive routes for the fermentation of sugars or hydrolyzed starch consist in the production of organic acids, such as lactic acid and butyric acid, solvents such as n-butanol and acetone, and polymers, such as the polyhydroxyalkanoates. Their routes of fermentation and purification are those traditionally known and do not integrate the inventive aspect of the present method, and in the description to follow there will only be referred the process of purification of the ethanol, for illustrative purposes.

In the case of the production of ethanol, the must originated from the fermentation step is then subjected to a distillation process for the production of hydrated ethanol. Optionally, this ethanol may be subjected to one of the processes known in the art for drying and obtainment of anhydrous alcohol.

The ethanol thus obtained may be used as fuel in vehicles or may alternatively be directed to the production of chemical alcohol derivatives. Among such derivatives, the chemical alcohol ethylene is worth pointing out in the context of the present integrated method. The ethylene can be obtained by dehydration of the ethanol using known processes, such as those described in the study "Ethylene from Ethanol", Harold W. Scheeline and Ryoji Itoh, PEP Review 79-3-4, January 1980, SRI International, in patent documents Nos. U.S. Pat. No. 4,232,179, U.S. Pat. No. 4,234,752, U.S. Pat. No. 4,396,789 and U.S. Pat. No. 4,529,827 and in patent application No. WO 2004/078336.

One characteristic held in common by the dehydration processes is the generation of water as by-product thereof. The water is a natural asset that is becoming increasingly scarce. The availability thereof in certain regions of the planet, even in some areas used for the production of certain types of renewable agricultural raw materials, is increasingly valued and its use should be managed to avoid losses thereof and to reutilize some volumes currently present in effluent streams.

Additionally, the reutilization of water obtained as a by-product of the dehydration of ethanol and other steps of the method according to the present invention constitutes another characteristic of the present integrated method, as will be explained below.

The residues of renewable natural raw materials preferably used in the method for the production of one or more olefins according to the present invention originate from sugarcane, from corn or from sorghum, such as, for example, sugarcane bagasse, sugarcane straw, corn straw and corn cobs and sorghum straw. Optionally, there may be used residues from other agricultural crops, urban or industrial residues, as well as residues originating from fishing, animal breeding or mining activities, such as, among others, beet, manioc, wheat or rice straw, peanut shells or coconut shells, wood kindling, wood chips or sawdust, charcoal, wax palm [*Carnaúba*] leaves, babassu palm [*Babacú*] residues, various types of grass, leaves and branches of soy plants, waste products of the process of production of vegetable oils, such as filtercakes obtained from the production of oils of soy, of castor oil plant and of other oleaginous plants, vegetable oils after use, animal fats, algae, recycled paper and paperboard, lignin and other residues from the paper and pulp industry originating from crops such as eucalyptus and pine, garbage, biogas derived from fermentation, glycerol, or residues containing glycerol, shellfish shells or bird feathers.

All these residues are capable of generating synthesis gas by means of biomass gasification processes known in the art, involving reaction in one or two stages in controlled conditions of temperature, pressure, oxygen concentration and moisture, resulting in the production of a mixture of carbon monoxide and hydrogen, whereto there may be added, if required, an additional amount of hydrogen for the formation of synthesis gas with the desired composition ($CO/H_2$).

One of the remarkable advantages of the process for production of the synthesis gas (gasification) resides is the fact that it can be applied to a very large range of raw materials, producing a synthesis gas that is both clean and devoid of ashes and other impurities.

Another method for producing this gas is the direct obtainment thereof by the reaction of water vapor with various materials of agricultural or fossil origin, such as lignocellulosic materials, residues of vegetable oils, coal, naphtha or natural gas.

In the case of residues of renewable natural raw materials rich in lignocellulosic materials, the latter can be previously subjected to decomposition by pyrolysis in an oxygen-free environment, whereby they are transformed into an oily residue that will be subsequently conveyed to the gasification process. The pyrolysis step may be integrated in the same reactor where the gasification takes place.

Normally, the pyrolysis occurs at temperatures between 100 and 700° C. and at pressures between $1\times10^2$ kPa and $1\times10^3$ kPa. The gasification occurs at higher temperatures and pressures, normally in the range of 700 to 1,500° C. and at pressures of $1\times10^2$ kPa to $2.5\times10^3$ kPa, with the injection of small amounts of oxygen, and if necessary, of steam, depending on the process used. Residues that are rich in vegetable oils and animal fats and the biogas are advantageously fed directly in the gasification step.

A small part of the material fed to the process is subject to total combustion to supply the energy required for the process. One of the characteristics of the integrated method according to the present invention consists in the reutilization of energy available from the streams leaving the gasification reactor at high temperatures in order to lower the residual humidity of the raw material being used to the levels deemed suitable for the gasification process, normally below 20% by weight of water, after being used to preheat the charge in the pyrolysis and gasification reactors. The processes used for pyrolysis and gasification are not critical in the present context, since there may be used any of the processes known in the art.

One possible complementary source for the production of synthesis gas consists in the reutilization of the carbon dioxide obtained as a by-product of the gasification or resulting from alcoholic fermentation, which can take place in two manners. In the first manner, the carbon dioxide is reduced to carbon monoxide by reacting the same with hydrogen, preferably in the presence of catalysts of the types of aluminosilicate, ferric oxide, potassium carbonate, tungsten sulphide, iron, nickel, cobalt, among others. Depending on the catalyst used, the reaction for reducing the carbon dioxide occurs at temperatures between 300 and 800° C. and at pressures between $1\times10^2$ kPa and $1\times10^4$ kPa. The hydrogen used may have various origins, such as the hydrogen obtained as a by-product in the processing of crude oil and natural gas, the hydrogen obtained as a by-product of the production of chlorine, or preferably, the hydrogen obtained by a water electrolysis reaction. This electrolysis presents the advantage of additional production of high-purity oxygen, which may be used in the gasification process. The water to be subjected to electrolysis is ideally the water obtained as a by-product in the reactions of the present method. In the second manner, the reutilization of the carbon dioxide occurs by means of the reduction thereof with organic materials containing carbon, oxygen and hydrogen, catalyzed with alkaline metal carbonates, at a temperature in the range of 550 to 1,100° C. and at pressures between $4\times10^2$ kPa and $1.5\times10^4$ kPa. Among these organic substances, there is pointed out the use of carbonaceous materials originated from agricultural raw materials, such as charcoal.

In the present method, the synthesis gas is used for the production of methanol, employing any of the known technologies used in large capacity plants (over 1 million tons/year of methanol).

The thus obtained methanol is used for the formation of propylene, directly or indirectly from the intermediate dimethyl ether, using known technologies, such as those described in U.S. Pat. No. 4,929,780, EP 448000 and U.S. Pat. No. 6,534,692.

Depending on the process conditions (temperature, recycles) and the catalyst used, the propylene may be obtained with high purity and high yield or may generate ethylene and butylene as co-products. The total amount of ethylene and propylene produced presents a global carbon yield between 60 and 90% by weight relatively to the initial methanol fed to the process. The propylene to ethylene ratio is also controlled, and there may be obtained almost pure propylene or ethylene:propylene ratios of up to 1.5:1. Additionally, there may also be obtained small amounts of butylene in relation to those two monomers. One other characteristic of this step consists in the fact that there are produced, as additional by-products, streams with characteristics similar to those of natural gas, LPG (Liquefied Petroleum Gas) and gasoline, that may be used to supply energy to the process and/or for transporting raw materials and products or may even be able to be recycled for the gasification step. The hydrocarbons thus produced are separated by distillation into the various streams of interest.

The reaction for transformation of methanol and/or dimethyl ether into propylene may comprise the use of one or more reactors arranged in series, configuring a process by stages, with the various recycle streams, also separated in the distillation step, being fed back to these stages according to the composition thereof. The catalysts used in the olefin-forming reaction from methanol, dimethyl ether or mixtures thereof comprise, for example, zeolites of the aluminosilicate, borosilicate and ferrosilicate types. Other suitable types of catalysts are highly crystalline metallic aluminophosphates where the preferred metals used may be silicon, magnesium, zinc, iron, cobalt, nickel, manganese, chromium and mixtures thereof. If it is intended to obtain high levels of conversion into propylene, there should be used as catalysts aluminosilicate-based zeolites of the Pentasil type, as described in patent No. EP 448000. The methanol and/or the dimethyl ether may be fed back to the reactor in anhydrous state or there may be preferably used water as the diluent, at a ratio between 0.1:1 and 2:1 by weight of water. The reaction temperature varies between 250 and 800° C., preferably between 300 and 550° C., and the required pressure may vary between 10 and 100 kPa, depending on the type of catalyst employed.

One important characteristic of the production of propylene and its co-products (ethylene/butylene) from methanol is that in this step there is also obtained water as a by-product. The water thus obtained is recovered by phase separation after cooling. Similarly to the water obtained as a by-product from the process of dehydration of ethanol, this water, that is the by-product from the propylene formation reaction, presents a high degree of purity and can be used in several steps of the method according to the present invention, such as in the extraction of sugarcane juice, to adjust the concentration of the juice for fermentation, or in the electrolysis of the water for the production of hydrogen useful to reduce the carbon dioxide and oxygen used in the gasification reaction.

Therefore, the reutilization of the water and carbon dioxide generated as by-products in the processes according to the present invention constitutes an additional characteristic of the present integrated method.

In addition, since the propylene production route contemplates two steps that are conducted at high temperatures (the gasification and the formation of propylene and other olefins from methanol and/or from dimethyl ether), the output streams of these process steps may be advantageously used to preheat streams already present in this route from lignocellulosic materials or in processing the sugarcane and the corn into the derivatives thereof, like sugar or starch, ethanol and ethylene. Preferably the output stream from the gasification reactor can be used to heat the charge of methanol and/or dimethyl ether fed to the reactors of formation of propylene and other olefins or to heat the charge of ethanol fed to the dehydration reactors. Additionally, the output stream of the last stage of the reaction system for formation of propylene and other olefins may be used to preheat and also to remove part of the water contained in the bagasse and straw of the sugarcane, or in the leaves, the culm or the cob of the corn plant, or in other biomasses with high moisture content, adjusting the humidity value to the concentration required for the pyrolysis process or for the gasification process.

Therefore, according to the preferred embodiment of the present invention, the integration and reutilization of the various streams derived from the processing of the sugarcane and/or corn, such as water, carbon dioxide, bagasse, corn cobs and straw generated as by-products in distinct steps, as well as the energy integration with recovery of heat from the various hot streams to heat colder streams, renders the use of lignocellulosic materials as raw materials economically feasible for the production of olefins, particularly propylene, and optionally ethylene and butylene.

The propylene, the ethylene and the butylene generated by the methods according to the present invention can be used for the obtainment of their known derivatives, preferably for the production of polypropylene and its copolymers and of polyethylene and its copolymers, resulting in polymers whose composition includes, when there is applied the most preferred embodiment of the present invention using only raw materials and residues from renewable natural sources, 100% carbon from renewable natural sources, as determined by the test method according to the ASTM D 6866-06 standard. One other complementary alternative consists in the use of other raw materials of non-natural (fossil) origin for the production of synthesis gas, such as for example, naphtha, natural gas, coal, recycled plastics and combustion gas from thermoelectrical power generation plants, among others, provided that the end products (olefins and their known derivatives, as well as polymers such as polyethylene and its copolymers, polypropylene and its copolymers, and PVC) include at least 50%, and preferably at least 80%, of carbon from a renewable natural source, as determined by the test method according to the ASTM D 6866-06 standard.

EXAMPLES

In order to provide a better understanding of the present invention and to evidence the technical progress having been achieved, there will now be presented the results of two examples considering a method for the obtainment of methanol from the processing of sugarcane and subsequent dehydration of the thus produced ethanol in order to produce ethylene. In Comparative Example 1 there has been contemplated only the production of ethylene by means of dehydration of ethanol. In Example 1, according to the present invention, there has been contemplated, in addition to the production of the said ethylene, the production of propylene from the residues derived from the process of production of the ethanol.

To facilitate the understanding of this description, the mass balance in both examples is relative to the use of 1,000 tons of sugarcane as raw material. All the percentages indicated in the examples are weight percentages.

Comparative Example 1

Using a mechanical harvester, there were harvested 1,000 tons of sugarcane containing 13.0% fermentable sugars (sucrose, glucose and fructose), 13.7% bagasse and 14.0% leaves and plant tips. The bales, containing the total amount of sugars and bagasse, were placed on specific flatbed loaders and 100% of the leaves and tips of the sugarcane plants were dispersed over the soil forming a dead cover for the protection of the soil. The bales were transported to the distilling facility.

Upon being received at the distilling facility, the bales were subjected to a preparation process, whereby they were chopped in small pieces and fed to an assembly comprised of six sets of three-roll crusher mills arranged in series. In order to aid the extraction of sugar, there were fed 300 cubic meters of water in counter current. At the end of the crushing, there were obtained 274 tons of bagasse, with a moisture content of 49%, 5% of ashes and 0.6% of residual sugars, and 826 tons of sugarcane juice containing 14.9% fermentable sugars. A small amount of water was lost by evaporation.

An amount corresponding to 70% of the bagasse was burned in boilers at a pressure of 65 bar to supply the electrical and thermal energy required by the processes of crushing of the sugarcane and production of the ethanol. The remaining 82 tons of bagasse could be commercialized for other industries or for use in cattle feeding.

The sugarcane juice was subjected to a conventional process of filtration, washing of the filtercake and pH adjustment, whereupon were obtained 880 tons of juice comprising 14% fermentable sugars. The juice was then fed into fermentation vats in the form of batches fed in the presence of inoculated *Saccharomyces cerevisiae*. Upon completion of the fermentation there had been produced 802 tons of a fermented must comprising 7.2% ethanol. After distillation, the fermented must yielded 62.2 tons of hydrated ethanol with 92.8% purity. In the process of fermentation, an amount of 58 tons of carbon dioxide, together with the water entrained in the emission of this gas, was launched into the atmosphere.

The ethanol thus produced was then fed to a dehydration system comprising 3 adiabatic reactors arranged in series, each having a fixed bed using gamma-alumina as catalyst. Together with the 62.2 tons of hydrated ethanol, there were fed to the reactors 135 tons of steam required by the adiabatic process. Since the dehydration reaction is endothermic, in order to achieve the desired temperature of 470° C. at the inlet of each of the three reactors, the mixture of hydrated ethanol and steam was preheated in kilns burning natural gas. The output stream of the third reactor was subjected to processes of purification and drying, and there were finally produced 34.1 tons of polymer-grade ethylene. Upon removal and treatment of the impurities obtained as by-products of the dehydration reaction (ether, ester, unreacted ethanol) there were recovered 154 tons of water.

At the end of the process, the carbon content of the ethylene corresponded to approximately 18% by weight relative to the carbon initially present in the sugarcane.

Example 1

In EXAMPLE 1 there is contemplated the production of ethanol and the dehydration thereof to produce ethylene from sugarcane, integrated with the production of propylene from residues originated from the processing of the sugarcane. All the percentages indicated herein are weight percentages.

Using a mechanical harvester, there were harvested 1,000 tons of sugarcane containing 13.0% fermentable sugars (sucrose, glucose and fructose), 13.7% bagasse and 14.0% leaves and plant tips. The bales, containing the total amount of sugars and bagasse, were placed on specific flatbed loaders and 50% of the leaves and tips of the sugarcane plants were placed on auxiliary flatbed loaders. The remaining 50% of the leaves and tips of the sugarcane plants, that constitute the sugarcane straw, were dispersed over the soil forming a dead cover to preserve the moisture thereof. The bales and the leaves together with the plant tips were transported to the distilling facility.

Upon being received at the distilling facility, the bales were subjected to a preparation process, whereby they were chopped in small pieces and fed to an assembly comprised of six sets of three-roll crusher mills arranged in series. In order to aid the extraction of sugar, there were fed 300 cubic meters of water in counter current. A part of this water was recycled from the ethylene and propylene processes described below. At the end of the crushing, there were obtained 274 tons of bagasse, with a moisture content of 49%, 5% of ashes and 0.6% of residual sugars, and 826 tons of sugarcane juice containing 14.9% fermentable sugars. A small amount of water was lost by evaporation.

The portion of 50% of leaves and tips carried to the distilling facility, which constitutes the sugarcane straw, corresponded to a total of 96 tons with 27% moisture content and 4% of ashes.

An amount corresponding to 70% of the bagasse was burned in boilers at a pressure of 65 bar to supply the electrical and thermal energy required by the processes of crushing of the sugarcane and production of the ethanol.

The sugarcane juice was subjected to a conventional process of filtration, washing of the filtercake and pH adjustment, whereupon were obtained 880 tons of juice comprising 14% fermentable sugars. The juice was then fed into fermentation vats in the form of batches fed in the presence of inoculated *Saccharomyces cerevisiae*. Upon completion of the fermentation there had been produced 802 tons of a fermented must comprising 7.2% ethanol. After distillation, the fermented must yielded 62.2 tons of hydrated ethanol with 92.8% purity. In the process of fermentation, an amount of 56 tons of carbon dioxide was recovered upon drying.

The ethanol thus produced was then fed to a dehydration system comprising 3 adiabatic reactors arranged in series, each having a fixed bed using gamma-alumina as catalyst. Together with the 62.2 tons of hydrated ethanol, there were fed to the reactors 135 tons of steam required by the adiabatic process. Since the dehydration reaction is endothermic, in order to achieve the desired temperature of 470° C. at the inlet of each of the three reactors, the mixture of hydrated ethanol and steam was preheated in kilns using the heat present in the output stream from the gasifiers as described below, in addition to the burning of the LPG obtained as a by-product from the formation of propylene. Eventually, the supply of additional heat for this step could be provided by burning a complementary fuel such as natural gas. The output stream from the third reactor was subjected to processes of purification and drying, and there were finally produced 34.1 tons of polymer-grade ethylene. Upon removal and treatment of the impurities obtained as by-products of the dehydration reaction (ether, ester, unreacted ethanol . . . ) there were recovered 154 tons of water to be recycled to the process.

The excess bagasse and straw corresponded to a total 178 tons with 37% average moisture content. These two residues derived from the production of ethanol were initially subjected to partial drying in vessels that were heated indirectly by air, with the heat being provided by the effluent streams from the reactors of production of propylene via methanol as described below. Eventually, there may be used the effluent streams from the reactors of production of ethylene via dehydration of ethanol.

After being previously dried, the mixture of bagasse and straw with about 15% residual moisture content was heated to 150° C. in the absence of air. The pyrolysis vapors thus obtained were then fed to a gasification reactor together with a small amount of oxygen required to maintain the temperature at 1,200° C. This hot stream of synthesis gas generated at the outlet of the reactor was used to preheat part of the mixture of ethanol and steam fed in the dehydration reactors, as mentioned before. The carbon dioxide formed in the gasification process was reduced to carbon monoxide with the addition of hydrogen into the reactor. The synthesis gas thus obtained was used to produce 93 tons of methanol.

Thereafter, the methanol was converted to dimethyl ether, and was fed to a reactor system that makes use of the catalysts with the technology described in patent document No. EP448000. Upon distillation, there were recovered 30 tons of polymer-grade propylene, in addition to 8 tons of gasoline, 3 tons of LPG and 52 tons of water for recycling. The burning of the LPG thus obtained was further used to supply energy to preheat the charge of the ethanol dehydration reactors.

By means of the reaction with hydrogen, it was further possible to transform the carbon dioxide obtained in the fermentation into additional synthesis gas by means of a reduction reaction. The synthesis gas thus obtained enabled the generation of an additional amount of 14 tons of propylene, thus providing a total 44 tons of this olefin.

At the end of the process, the carbon contained in the ethylene and propylene thus obtained corresponded to approximately 42% in mass in relation to the carbon initially present in the sugarcane.

Example 2

A sample of the propylene obtained in EXAMPLE 1 was mass-polymerized in a reactor with 4 liters of capacity, at 70° C. and at a pressure of 30 bar, using a Ziegler-Natta catalyst. After 2 hours of reaction, there were produced 310 grams of polypropylene.

The polymer thus obtained was subjected to a test to determine its carbon-14 content following the test method prescribed in the ASTM D 6866-06 standard. The result of the test indicated that the polymer had a natural carbon content equal to 100%.

The invention claimed is:

1. A method for the production of one or more olefins consisting of the following steps: (i) gasification reaction of lignocellulosic materials and/or other organic components contained in residues from harvesting of a renewable natural agricultural raw material, resulting in the production of a mixture of carbon monoxide and hydrogen (synthesis gas); (ii) formation of methanol from the synthesis gas generated in step (i); and (iii) transformation of the methanol obtained in step (ii), directly or indirectly from an intermediate dimethyl ether, into one or more olefins, wherein it is integrated with a method of processing a renewable natural agricultural raw material into ethanol or ethylene, so that at least a part of the lignocellulosic residue generated in the method of processing the renewable natural agricultural raw material is directed to the gasification reaction of step (i), together with the following:

(a) the carbon dioxide generated in the method of processing the renewable natural agricultural raw material is reduced to carbon monoxide by means of a reaction with hydrogen or with organic materials containing carbon, oxygen and hydrogen, generating a complementary amount of synthesis gas, which is directed to step (ii) of methanol formation;

(b) the water generated as a by-product in step (iii) and, occasionally, also in the method of processing the renewable natural agricultural raw material is reused in at least the extraction of sugarcane juice; and (c) the streams leaving the gasification reactor and those leaving the step of formation of olefins from methanol provide the necessary heat to reduce the residual moisture of the residue of the renewable natural raw material to the levels required for the gasification reaction, or to preheat the charge in the gasification reactor, the charge of methanol and/or dimethyl ether, fed into the dehydration reactor.

2. A method as claimed in claim 1, wherein the one or more olefins comprises propylene, and optionally, ethylene and butylene.

3. A method as claimed in claim 1, wherein the gasification reaction of step (i) takes place at temperatures in the range of 700 to 1,500° C. and at pressures of 1 to 25 bar.

4. A method as claimed in claim 1, wherein step (i) is optionally preceded by the process of pyrolysis of the residues of the renewable natural raw material in the absence of oxygen.

5. A method as claimed in claim 4, wherein the pyrolysis process takes place at temperatures between 100 and 700° C. and at pressures between 1 and 10 bar absolute.

6. A method as claimed in claim 1, wherein the transformation of the methanol into one or more olefins of step (iii) takes place at a temperature between 250 and 800° C. and at a pressure between 10 and 100 kPa.

7. A method as claimed in claim 1, wherein the residue of the renewable natural agricultural raw material has a high content of one or more components among sugars, starch, lignocellulosic components, oils, fats or other organic materials.

8. A method as claimed in claim 7, wherein the harvesting and processing residues of the renewable natural agricultural raw material originates from sugarcane, corn or sorghum, such as sugarcane bagasse and straw, corn straw and cobs, and sorghum straw.

9. A method as claimed claim 7, wherein the processing method comprises the fermentation of the sugar or the starch, provided that the latter is previously hydrolyzed, found in the renewable natural agricultural raw material, resulting in the production of ethanol and carbon dioxide.

10. A method as claimed in claim 9, wherein in the fermentation step there is used the yeast *Saccharomyces cerevisiae*.

11. A method as claimed in claim 9, wherein the must originated from the fermentation step is subjected to a process of distillation for the production of ethanol.

12. A method as claimed in claim 11, wherein the ethanol is dehydrated in order to obtain ethylene.

13. A method as claimed in claim 12, wherein the water generated in the method of processing the renewable natural agricultural raw material is obtained in the process of dehydration of the ethanol.

14. A method as claimed in claim 1, wherein the reduction of the carbon dioxide with hydrogen takes place at temperatures between 300 and 800° C. and at pressures between 1 and 100 bar.

15. A method as claimed in claim 1, wherein the reduction of the carbon dioxide with organic materials takes place at temperatures in the range of 550 to 1,100° C. and at pressures between 4 and 150 bar.

16. A method as claimed in claim 1, wherein the water can be used to extract the sugarcane juice, to adjust the concentration of the juice for fermentation or in the electrolysis of the water for generating hydrogen, which is useful to reduce the carbon dioxide, and for generating oxygen, which is employed in the gasification reaction.

17. A method as claimed in claim 1, wherein other residues, such as urban or industrial residues, or residues originating from fishing, animal breeding or mining activities, may be added to the residue generated in the method of processing the renewable natural agricultural raw material, provided that they can be subjected to gasification.

18. A method as claimed in claim 1, wherein the amount of produced olefins corresponds to a global carbon yield in relation to the methanol of between 65 and 90%, or more.

19. An integrated method of utilizing a renewable natural agricultural raw material for the production of one or more olefins consisting of the following steps:
(i) harvesting sugarcane, wherein at least 30% of residual harvesting lignocellulosic materials, including leaves and straw, are subjected to the following steps and the remaining residual harvesting lignocellulosic materials are utilized for soil coverage;
(ii) gasification reaction of subjecting residual harvesting lignocellulosic materials and other organic components contained in residue of a renewable natural agricultural raw material to a gasification reaction, resulting in the production of a mixture of carbon monoxide and hydrogen (synthesis gas);
(iii) formation of methanol from the synthesis gas generated in step (ii); and
(iv) converting the methanol obtained in step (iii), directly or indirectly from the intermediate dimethyl ether, into one or more olefins, wherein it is integrated with a method of processing sugarcane into ethanol or ethylene, so that the residual lignocellulosic materials generated in the method of processing sugarcane, including sugarcane bagasse, is directed to the gasification reaction of step (ii) and the remaining residual lignocellulosic materials generated in the method of processing sugarcane is used as a source of energy, together with the following:
(a) the carbon dioxide generated in the method of processing sugarcane is reduced to carbon monoxide by means of a reaction with hydrogen or with organic materials containing carbon, oxygen and hydrogen, generating a complementary amount of synthesis gas, which is directed to step (iii) of methanol formation;
(b) the water generated as a by-product in step (iv) and, occasionally, also in the method of processing sugarcane into ethylene is reused in at least the extraction of sugarcane juice; and
(c) the streams leaving the gasification reactor and those leaving the step of formation of olefins from methanol provide the necessary heat to reduce the residual moisture of the residue of sugarcane to the levels required for the gasification reaction, or to preheat the charge in the gasification reactor, the charge of methanol and/or dimethyl ether, fed into the dehydration reactor.

20. The integrated method as claimed in claim 19, wherein greater than 50% of residual harvesting lignocellulosic materials, including leaves and straw, are subjected to steps (ii) to (iv).

* * * * *